(12) United States Patent
Gofman

(10) Patent No.: US 10,928,379 B2
(45) Date of Patent: Feb. 23, 2021

(54) BIOSENSOR CALIBRATION CODING SYSTEMS AND METHODS

(71) Applicant: Ascensia Diabetes Care Holdings AG, Basel (CH)

(72) Inventor: Igor Gofman, Croton-on-Hudson, NY (US)

(73) Assignee: Ascensia Diabetes Care Holdings AG, Basel (CH)

( * ) Notice: Subject to any disclaimer, the term of this patent is extended or adjusted under 35 U.S.C. 154(b) by 0 days.

(21) Appl. No.: 16/659,258

(22) Filed: Oct. 21, 2019

(65) Prior Publication Data

US 2020/0103393 A1    Apr. 2, 2020

Related U.S. Application Data

(60) Continuation of application No. 16/420,990, filed on May 23, 2019, now Pat. No. 10,488,395, which is a (Continued)

(51) Int. Cl.
*G01N 33/48* (2006.01)
*G01N 33/487* (2006.01)
(Continued)

(52) U.S. Cl.
CPC ....... *G01N 33/48771* (2013.01); *G01N 21/78* (2013.01); *G01N 21/8483* (2013.01);
(Continued)

(58) Field of Classification Search
CPC .......... G01N 27/3272; G01N 27/3273; G01N 27/3274; G01N 33/48771; G01N 27/3275;
(Continued)

(56) References Cited

U.S. PATENT DOCUMENTS

| 3,907,503 A | 9/1975 | Betts et al. |
| 5,780,304 A | 7/1998 | Matzinger et al. |

(Continued)

FOREIGN PATENT DOCUMENTS

| EP | 1 288 653 A1 | 6/2011 |
| WO | WO2009/061568 A1 | 5/2009 |
| WO | WO 2010/048277 A2 | 4/2010 |

OTHER PUBLICATIONS

International Search Report, PCT/US2015/019020, dated May 19, 2015 (4 pages).

(Continued)

*Primary Examiner* — Michael P Stafira
(74) *Attorney, Agent, or Firm* — Nixon Peabody LLP

(57) ABSTRACT

A test sensor (100) for determining an analyte concentration in a biological fluid comprises a strip including a fluid receiving area (128) and a port-insertion region (126). A first row of optically transparent (132) and non-transparent positions forms a calibration code pattern (130) disposed within a first area of the port-insertion region (126). A second row of optically transparent (142) and non-transparent positions forms a synchronization code pattern (140) disposed within a second area of the port-insertion region (126). The second area is different from the first area. The synchronization code pattern (140) corresponds to the calibration code pattern (130) such that the synchronization code pattern (140) provides synchronization of the serial calibration code pattern (130) during insertion of the port-insertion region (126) into the receiving port of the analyte meter.

20 Claims, 8 Drawing Sheets

Related U.S. Application Data division of application No. 15/123,334, filed as application No. PCT/US2015/019020 on Mar. 5, 2015, now Pat. No. 10,330,666.

(60) Provisional application No. 61/949,587, filed on Mar. 7, 2014.

(51) Int. Cl.
| | | |
|---|---|---|
| *G01N 21/84* | (2006.01) | |
| *G01N 21/78* | (2006.01) | |
| *G01N 27/327* | (2006.01) | |
| *G01N 33/49* | (2006.01) | |
| *G01N 21/77* | (2006.01) | |

(52) U.S. Cl.
CPC ..... *G01N 27/3272* (2013.01); *G01N 27/3274* (2013.01); *G01N 33/49* (2013.01); *G01N 2021/7759* (2013.01); *G01N 2021/7786* (2013.01); *G01N 2201/127* (2013.01)

(58) Field of Classification Search
CPC .. G01N 27/307; G01N 33/5438; G01N 21/78; G01N 27/3271; G01N 27/327; G01N 27/3277; G01N 2800/04; G01N 27/12; G01N 27/3276; G01N 33/4875; G01N 33/48757; G01N 2021/7759; G01N 2333/904; G01N 27/226; G01N 27/26; G01N 27/27; G01N 27/40; G01N 33/48785; G01N 33/48792; G01N 33/49; G01N 33/66; G01N 33/6893; G01N 33/723; G01N 33/84; G01N 2021/7786; G01N 21/8483; G01N 2333/902; G01N 27/3278; G01N 27/4145; G01N 2800/52; G01N 33/487; G01N 33/4925; G01N 33/53; G01N 33/6806; G01N 33/6812; G01N 33/92; G01N 2021/775; G01N 2035/00851; G01N 21/6428; G01N 21/75; G01N 2201/127; G01N 2333/4703; G01N 2333/4712; G01N 2333/4727; G01N 2333/90235; G01N 2333/90622; G01N 2405/04; G01N 2610/00; G01N 27/02; G01N 27/021; G01N 27/028; G01N 27/22; G01N 27/308; G01N 27/4163; G01N 27/4168; G01N 27/48; G01N 2800/16; G01N 33/48707; G01N 33/48778; G01N 33/492; G01N 33/493; G01N 33/50; G01N 33/5094; G01N 33/521; G01N 33/523; G01N 33/525; G01N 33/5302; G01N 33/54386; G01N 33/558; G01N 33/57442; G01N 33/57449; G01N 33/57488; G01N 33/6803; G01N 33/6872; G01N 33/98

See application file for complete search history.

(56) References Cited

U.S. PATENT DOCUMENTS

| | | |
|---|---|---|
| 5,945,341 A | 8/1999 | Howard, III |
| 6,488,891 B2 | 12/2002 | Mason et al. |
| 6,814,844 B2 | 11/2004 | Bhullar et al. |
| 7,236,812 B1 | 6/2007 | Ballerstadt et al. |
| 7,593,097 B2 | 9/2009 | Robinson et al. |
| 7,780,827 B1 | 8/2010 | Bhullar et al. |
| 7,809,512 B2 | 10/2010 | Perry |
| 7,822,557 B2 | 10/2010 | Chen et al. |
| 7,847,946 B2 | 12/2010 | Krauth |
| 7,896,819 B2 | 3/2011 | Rebee et al. |
| 8,032,321 B2 | 10/2011 | Zhong |
| 8,101,062 B2 | 1/2012 | Deng |
| 8,128,803 B2 | 3/2012 | Barlag et al. |
| 8,206,564 B2 | 6/2012 | Schell et al. |
| 8,241,488 B2 | 8/2012 | Beer |
| 8,375,574 B2 | 2/2013 | Wang et al. |
| 8,413,886 B2 | 4/2013 | Creaven et al. |
| 8,420,404 B2 | 4/2013 | Diebold et al. |
| 8,424,763 B2 | 4/2013 | Charlton et al. |
| 8,515,516 B2 | 8/2013 | Kamath et al. |
| 2003/0207441 A1 | 11/2003 | Eyster et al. |
| 2003/0207454 A1 | 11/2003 | Eyster et al. |
| 2007/0077175 A1 | 4/2007 | Harttig |
| 2007/0081920 A1 | 4/2007 | Murphy et al. |
| 2007/0110615 A1 | 5/2007 | Neel |
| 2007/0273928 A1 | 11/2007 | Robinson et al. |
| 2008/0034835 A1 | 2/2008 | Schell |
| 2008/0105024 A1* | 5/2008 | Creaven ............ G01N 33/48771 73/1.02 |
| 2009/0026094 A1 | 1/2009 | Deug et al. |
| 2010/0017165 A1 | 1/2010 | Zhong |
| 2010/0119414 A1 | 5/2010 | Eisenhardt et al. |
| 2010/0288841 A1 | 11/2010 | Ripley et al. |
| 2011/0198487 A1 | 8/2011 | Micinski et al. |
| 2012/0241318 A1 | 9/2012 | Neel et al. |
| 2013/0175344 A1 | 7/2013 | Watanabe |
| 2014/0045202 A1 | 2/2014 | Wang |

OTHER PUBLICATIONS

Written Opinion of the International Searching Authority, PCT/US2015/019020, dated May 19, 2015 (8 pages).

* cited by examiner

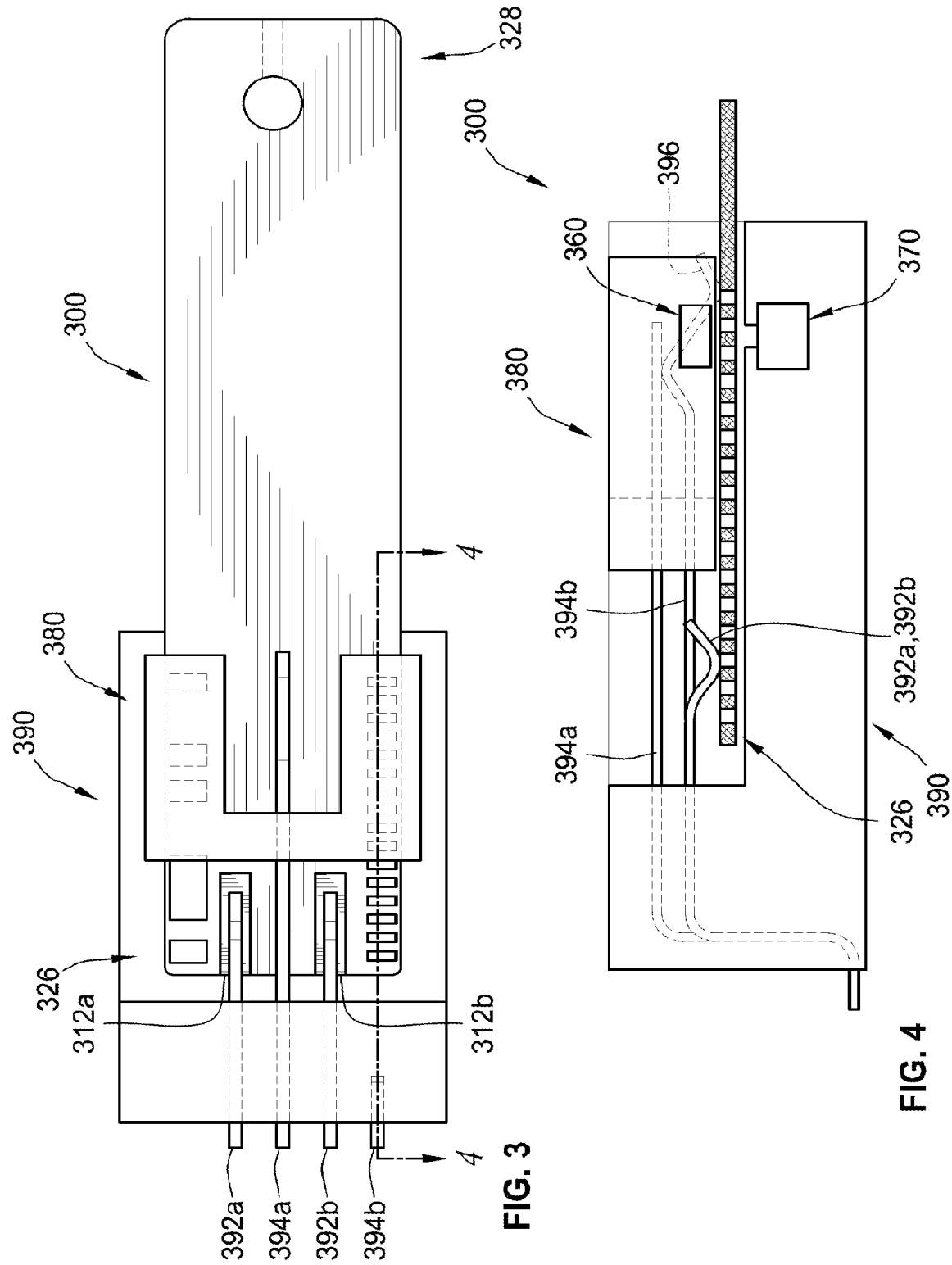

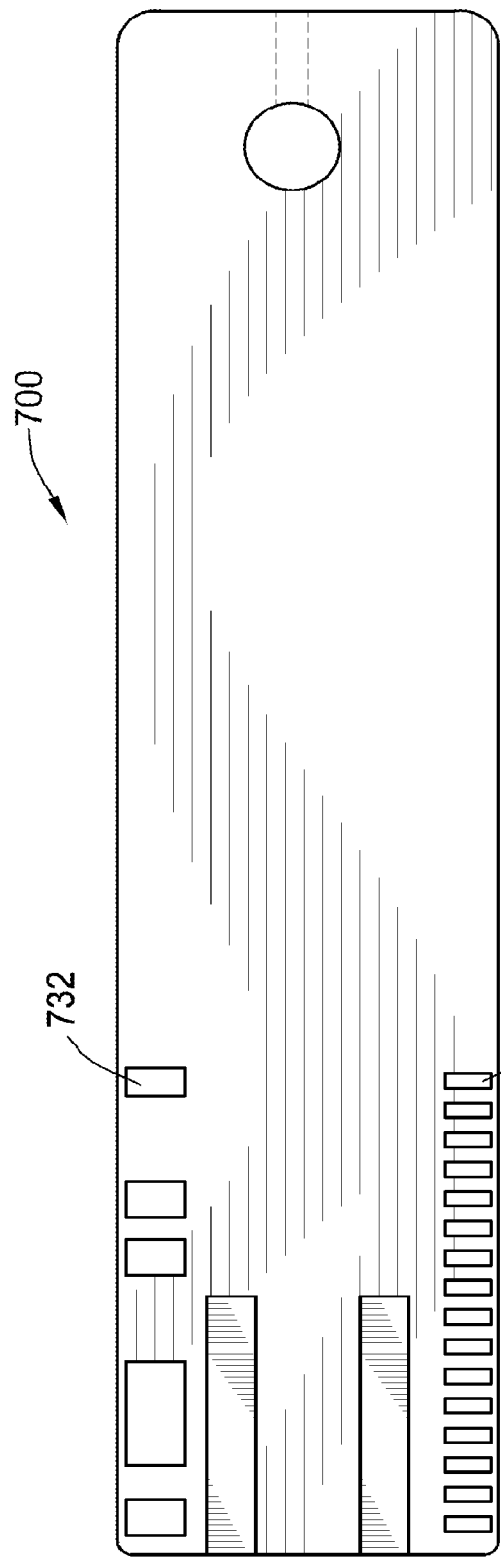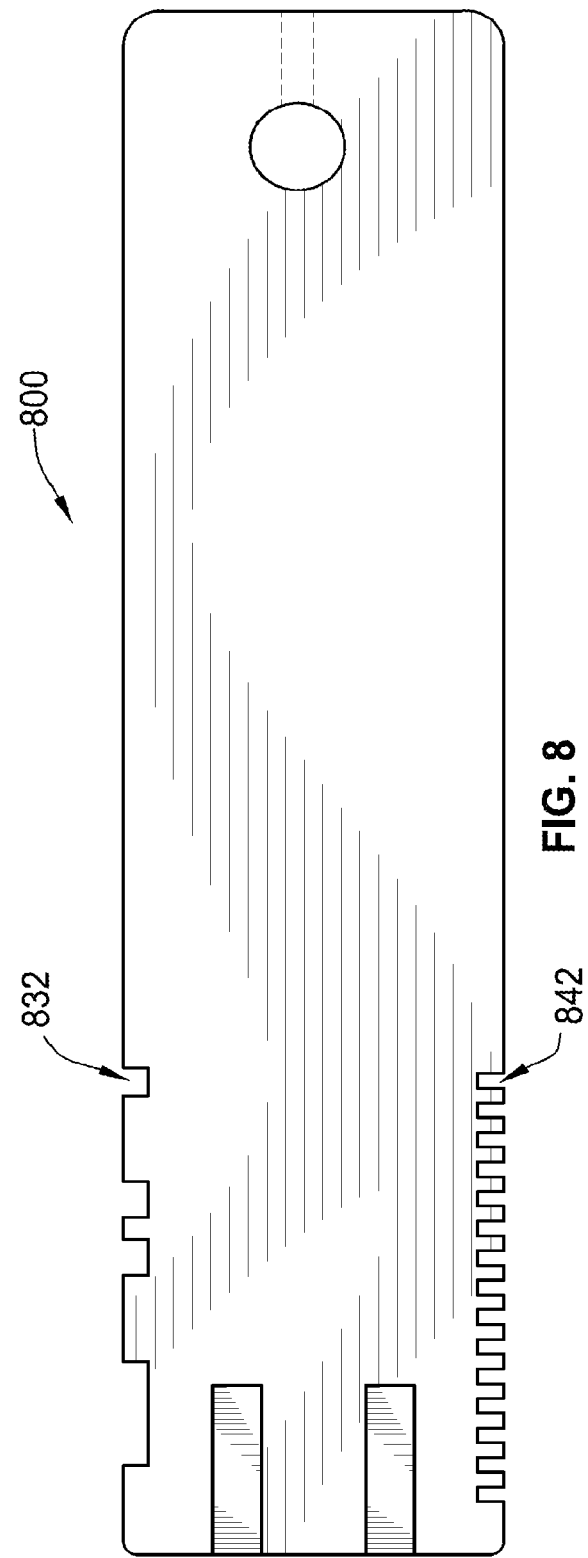

BIOSENSOR CALIBRATION CODING SYSTEMS AND METHODS

CROSS-REFERENCE TO RELATED APPLICATIONS

This application is a continuation of U.S. application Ser. No. 16/420,990, filed May 23, 2019, now allowed, which is a divisional of U.S. application Ser. No. 15/123,334, filed on Sep. 2, 2016, now U.S. Pat. No. 10,330,666, which is a U.S. National Stage of International Application No. PCT/US2015/019020, filed Mar. 5, 2015, which claims priority to and the benefits of U.S. Patent Application No. 61/949,587, filed Mar. 7, 2014, the contents of each of which are hereby incorporated by reference herein in their entireties.

FIELD OF THE INVENTION

The present invention generally relates to biosensors for determining analyte concentration of a fluid sample, and more particularly, to systems and methods of serial coding of biosensors to calibrate instruments that determine an analyte concentration of a fluid sample.

BACKGROUND OF THE INVENTION

The quantitative determination of analytes in body fluids is of great importance in the diagnoses and maintenance of certain physiological conditions. For example, lactate, cholesterol, and bilirubin should be monitored in certain individuals. In particular, determining glucose in body fluids is important to individuals with diabetes who must frequently check the glucose level in their blood to regulate the carbohydrate intake in their diets. The results of such tests can be used to determine what, if any, insulin or other medication needs to be administered. In one type of testing system, test sensors are used to test a fluid such as a sample of blood.

A test sensor contains biosensing or reagent material that reacts with blood glucose. The testing end of the sensor is adapted to be placed into the fluid being tested, for example, blood that has accumulated on a person's finger after the finger has been pricked. The fluid is drawn into a capillary channel that extends in the sensor from the testing end to the reagent material by capillary action so that a sufficient amount of fluid to be tested is drawn into the sensor. The fluid then chemically reacts with the reagent material in the sensor and the system correlates this to information relating an analyte (e.g., glucose) in a fluid sample.

Diagnostic systems, such as blood-glucose testing systems, typically calculate the actual glucose value based on a measured output and the known reactivity of the reagent-sensing element (test sensor) used to perform the test. The reactivity or lot-calibration information of the test sensor may be given to the user in several forms including a number or character that they enter into the instrument. One method includes using an element that is similar to a test sensor, but which was capable of being recognized as a calibration element by the instrument. The test element's information is read by the instrument or a memory element that is plugged into the instrument's microprocessor board for directly reading the test element.

There is an ongoing need for improved biosensors, especially those that may provide increasingly accurate and/or precise analyte concentration measurements. The systems, devices, and methods of the present invention overcome at least one of the disadvantages associated with encoding patterns on sensor strips used in biosensors.

SUMMARY OF THE INVENTION

According to one aspect of the present invention, a test sensor for determining an analyte concentration in a biological fluid comprises a strip including a fluid receiving area and a port-insertion region. A first row of optically transparent and non-transparent positions forms a calibration code pattern disposed within a first area of the port-insertion region. A second row of optically transparent and non-transparent positions forms a synchronization code pattern disposed within a second area of the port-insertion region. The second area is different from the first area. The synchronization code pattern corresponds to the calibration code pattern such that the synchronization code pattern provides synchronization of the serial calibration code pattern during insertion of the port-insertion region into the receiving port of the analyte meter.

According to another aspect of the present invention, a test sensor for determining an analyte concentration in a biological fluid comprises a strip including a fluid-receiving area and a port-insertion region. One or more electrical contacts are at least partially disposed within the port-insertion region. The electrical contacts are configured to align and electrically connect with sensor contacts of an analyte meter upon insertion of the port-insertion region into a receiving port of the analyte meter. A serial calibration code pattern is disposed within a first area of the port-insertion region. The serial calibration code pattern includes first optically transparent portions allowing light waves to be transmitted therethrough. A synchronization code pattern is disposed within a second area of the port-insertion region. The second area is different from the first area. The synchronization code pattern includes second optically transparent portions allowing light waves to be transmitted therethrough. The synchronization code pattern corresponds to the serial calibration code pattern such that the synchronization code pattern provides synchronization of the serial calibration code pattern during insertion of the port-insertion region into the receiving port of the analyte meter.

According to another aspect of the present invention, a biosensor system for determining an analyte concentration in a biological fluid comprises a measurement device including a processing unit connected to an optical pattern read device. The optical pattern read device includes one or more light sources, a first light sensor, and a second light sensor. A sensor strip includes sequential data coding patterns including first optically transparent openings and separate corresponding synchronization coding patterns including second optically transparent openings. The one or more light sources are configured to transmit light waves through the first and second optically transparent openings. The one or more light sources are at least partially positioned on a first side of the first and second optically transparent openings. The first light sensor is positioned on an opposite side of the first optically transparent openings and the second light sensor is positioned on an opposite side of the second optically transparent openings. The first light sensor and the second light sensor are configured to receive transmitted light waves from the one or more light sources. The light waves are transmitted by the one or more light sources and received by the first light sensor and the second light sensor while the sensor strip is being inserted into the measurement device such that light waves received by the second light sensor associated with the synchronization coding patterns provide synchronization for the light waves received by the first light sensor associated with the sequential data coding patterns.

According to yet another aspect of the present invention, a method for calibrating an analysis of an analyte in a biological fluid. The method includes the following acts: (a) transmitting light waves through first optically transparent openings in a test sensor including a first row of sequential optically transparent and non-transparent positions forming calibration coding patterns; (b) near simultaneous to act (a), transmitting light waves through second optically transparent openings in the test sensor including a second row of sequential optically transparent and non-transparent positions forming synchronization coding patterns that correspond to the calibration coding patterns; (c) receiving the light waves transmitted through the first optically transparent openings in a first light sensor; (d) receiving the light waves transmitted through the second optically transparent openings in a second light sensor; (e) generating a series of calibration code signals in response to light waves being received and not received by the first light sensor due to the optically transparent and non-transparent positions passing the first light sensor during the insertion of the test sensor into the analyte measuring device; (f) near simultaneous to act (e), generating a series of synchronization code signals in response to light waves being received and not received by the second light sensor due to the second row of sequential optically transparent and non-transparent positions passing the second light sensor during the insertion of the test sensor into the analyte measuring device, the series of synchronization code signals corresponding to the series of calibration code signals; (g) calibrating at least one correlation equation in response to the series of calibration code signals; and (h) determining an analyte concentration in response to the at least one calibrated correlation equation. The analyte concentration is determined by reacting the analyte in an electrochemical reaction that produces an output signal. The analyte concentration is calculated using the at least one calibrated correlation equation and the produced output signal.

Additional aspects of the invention will be apparent to those of ordinary skill in the art in view of the detailed description of various embodiments, which is made with reference to the drawings, a brief description of which is provided below.

BRIEF DESCRIPTION OF THE DRAWINGS

FIG. 3 illustrates a top view of a sensor strip with serial optical coding inserted into a sensor interface and optical pattern read device according to one embodiment.

FIG. 4 illustrates a side view of the sensor strip in FIG. 3 according to one embodiment.

FIGS. 7 and 8 illustrate sensor strips including optically transparent serial data coding patterns and synchronization coding patterns created by punching apertures into the sensor strip according to certain embodiments.

Figure 1:
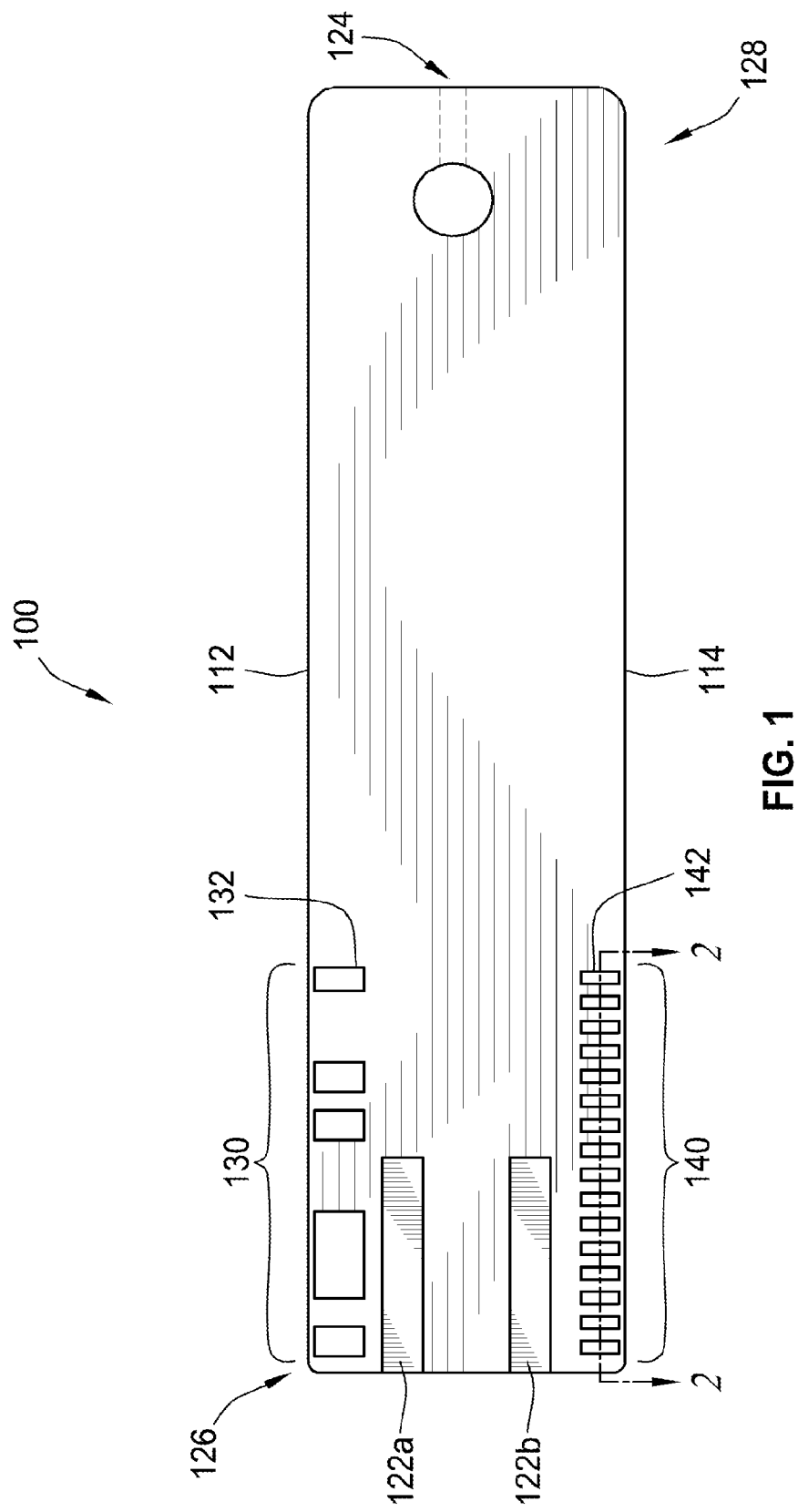
FIG. 1 illustrates a top view of a sensor strip with serial optical coding according to one embodiment.

While the invention is susceptible to various modifications and alternative forms, specific embodiments are shown by way of example in the drawings and are described in detail herein. It should be understood, however, that the invention is not intended to be limited to the particular forms disclosed. Rather, the invention is to cover all modifications, equivalents, and alternatives falling within the spirit and scope of the invention.

DETAILED DESCRIPTION

While this invention is susceptible of embodiment in many different forms, there is shown in the drawings and will herein be described in detail preferred embodiments of the invention with the understanding that the present disclosure is to be considered as an exemplification of the principles of the invention and is not intended to limit the broad aspect of the invention to the embodiments illustrated. For purposes of the present detailed description, the singular includes the plural and vice versa (unless specifically disclaimed); the word "or" shall be both conjunctive and disjunctive; the word "all" means "any and all"; the word "any" means "any and all"; and the word "including" means "including without limitation."

The present disclosure relates to improvements in sensors (e.g., sensor strips, biosensors, test sensors) for systems for determining analyte concentrations in fluid samples, such as biological samples (e.g., blood glucose samples). Sensors are used to collect analyte samples, such as fluid samples (e.g., blood sample, other biological fluid samples), and are inserted into an analyte concentration measurement device (e.g., blood glucose meter) where signals may be applied to the sample via the sensors as part of determining an analyte concentration of the fluid sample. Sensors are typically manufactured in batches that are calibrated at a manufacturing facility. Coding information may be applied to a sensors that can be read by or otherwise determined by an analyte concentration measurement device (e.g., blood glucose meter). In some aspects, the calibration information is received by the device following the insertion of the sensor into the measurement device that applies the test signal to the sample that was received on the sensor.

Calibration information can be used to adjust the analysis of the analyte concentration determination in response to one or more calibration parameters (e.g., manufacturing variations, sensor expiration date) that are encoded onto a sensor and read by an analyte concentration measurement device. A desirable aspect of the present disclosure is the ability to improve the accuracy of an analyte concentration measurement by allowing an increased amount of calibration information to be encoded onto a sensor. The increased amount of calibration information can then be read by the measurement device after a sensor is inserted into a sensor connector or sensor interface of the measurement device where an increased number of calibration codes are read and processed to correct a stored equation associated with a determination of an analyte concentration of a fluid sample.

The calibration codes are specific to and present on the sensor itself and can further include calibration parameters that take into account, for example, manufacturing variations, sensor strip expiration information, and other aspects that can be corrected for when determining an analyte concentration of a fluid sample.

Sensors, such as those used to test biological fluid samples (e.g., blood) can include generally rectangular dimensions ranging anywhere from about 0.1 to 0.5 inches (about 2.5 to 12.7 mm) wide by about 0.5 to 1.5 inches (about 12 to 38 mm) long. In some aspects, a top surface area of a flat test sensor can range anywhere from about 0.05 to 0.75 square inches (about 30 to 483 $mm^2$). Sensors typically include a fluid-receiving area and an area with contacts for electrically connecting the sensor to the analyte concentration measurement device. Based on the relatively small size of sensors for biological fluid sampling, such as sensors for determining blood glucose concentrations, there is a very limited amount of space to encode a sensor with calibration information that can be read from the sensor and used in determining an analyte concentration.

The application of parallel code patterns can be used for small surface areas on certain sensor strips. However, parallel coding has only a limited number of code variations (e.g., typically about eight for a sensor strip for biological fluids such as blood). Furthermore, parallel coding requires the insertion of the entire coding pattern into a sensor port of a measurement device so that the entire pattern is read at the same time. Serial code patterns can also be used and provide a higher number of code variations (e.g., up to fifteen for a sensor strip for biological fluids such as blood) than are typically available for parallel coding. However, serial coding typically requires a significant amount of space relative to the limited surface area available for coding on a test sensor, such as a typical test sensor used for biological fluid samples (e.g., blood glucose samples). For example, to increase the number of code variations using serial coding (e.g., more than fifteen), the length of a sensor strip would need to increase and a larger sensor port on a measurement device would be needed. It would be desirable to encode a sensor strip with a large number of different calibration codes to allow for greater accuracy of analyte concentration determinations, while limiting the area needed on a sensor strip to accommodate the calibration coding patterns. The present disclosure provides the ability to implement hundreds and even thousands of calibration codes within the very limited space of a sensor strip using optical methods where optically transparent coding patterns can be read with an optical pattern reading device. By allowing a larger number of calibration codes, the accuracy of analyte concentration measurements is increased as more factors can be used to correct the equation for calculating an analyte concentration. An increase in calibration codes allows for more sensor specific corrections such as variations in manufacturing or other sensor-specific factors (e.g., reagent characteristics, expiration date of sensor, batch number corrections) that, uncorrected, can cause a decrease in the accuracy of analyte concentration determinations.

Figure 2:
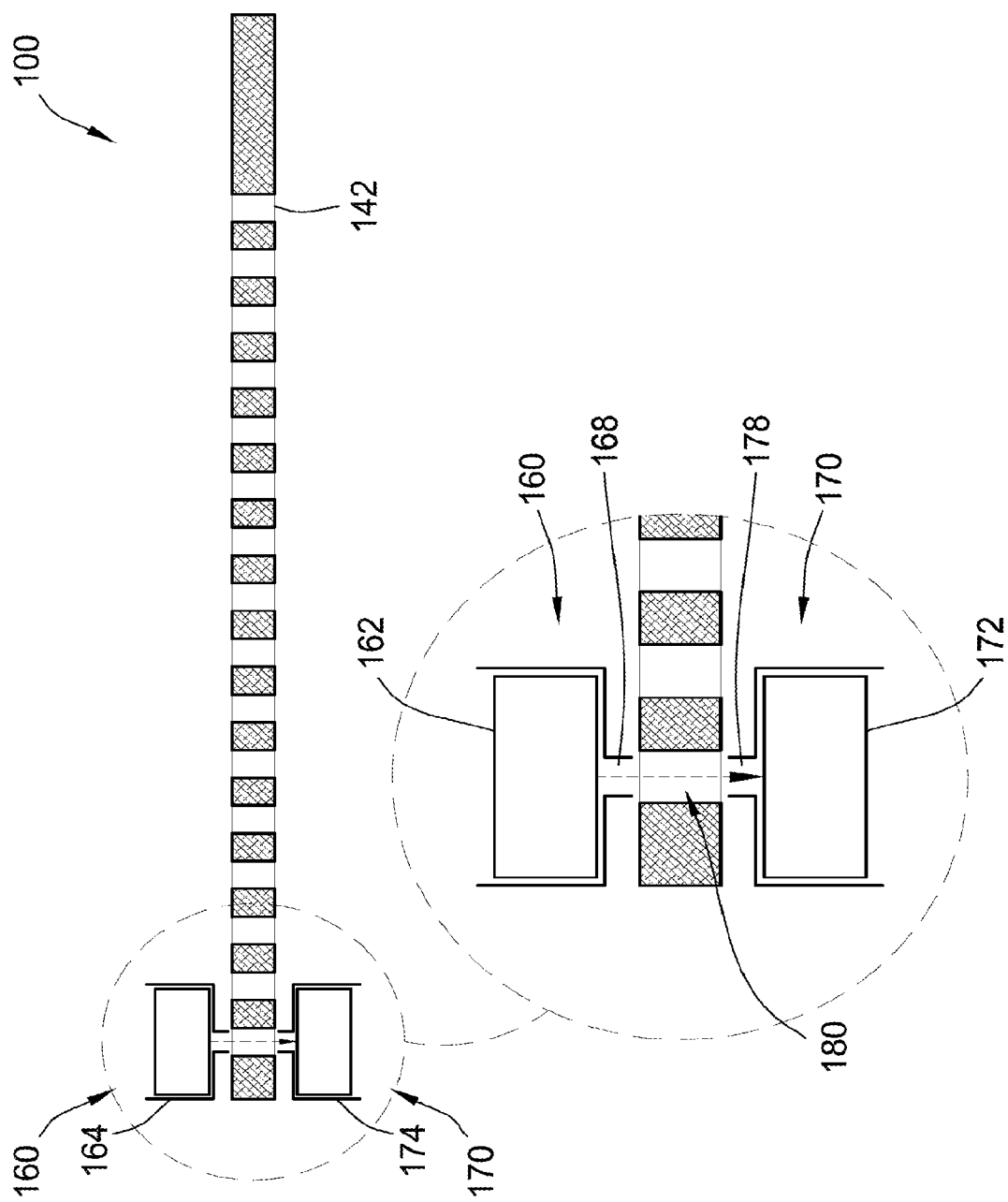
FIG. 2 illustrates a side view of a portion of the sensor strip in FIG. 1 along with aspects of an optical pattern read device according to one embodiment.

Turning now to FIGS. 1 and 2, a top view and side view of an exemplary biosensor 100 (e.g., test sensor, sensor strip) is illustrated that includes calibration coding. The exemplary biosensor 100 is depicted as a generally flat, elongated strip, though other shapes are contemplated (e.g., forked end, tapered end, trapezoidal portions, combinations of shapes). The biosensor includes a fluid-receiving area 128 and a port-insertion region 126. The fluid-receiving area 128 includes a channel 124 configured to receive fluid samples, such as sample of a biological fluid. The channel 124 may be sized such that capillary action pulls the fluid sample into the channel of the fluid-receiving area 128. The received fluid sample can then be tested to determine an analyte concentration using an instrument or meter after the port-insertion region 126 of the biosensor 100 is inserted into the instrument or meter.

It is contemplated that the non-limiting exemplary sensors described herein (e.g., biosensor 100) may be electrochemical test sensors. In such embodiments, an analyte meter may have optical, mechanical or optical aspects so as to detect the calibration information and electrochemical aspects to determine the analyte concentration of the fluid sample. While only a top view of the biosensor is illustrated in FIG. 1, such biosensors can include a base and a second layer (e.g., a lid) that assist in forming the channel 124. The biosensor 100 may also include a plurality of electrodes (not shown) such as a counter electrode, a working electrode, a trigger electrode, an underfill detection electrode, or a hematocrit electrode in the fluid-receiving area 128. The electrodes are coupled to conductive leads (not shown) that extend from the fluid-receiving area 128 to biosensor contacts 122*a*, 122*b* in the port-insertion region 126. The electrodes may be at least partially embedded between the base and lid and the conductive leads may extend within the base and lid of the biosensor from the electrodes to biosensor contacts 122*a*, 122*b* in the port-insertion region. It is contemplated that electrochemical test sensors other than those illustrated may be employed.

The fluid-receiving area 128 includes at least one reagent for converting the analyte of interest (e.g., glucose) in the fluid sample (e.g., blood) into a chemical species that is electrochemically measurable, in terms of the electrical current it produces, by the components of the electrode pattern. The reagent typically contains an enzyme such as, for example, glucose oxidase, which reacts with the analyte and with an electron acceptor such as a ferricyanide salt to produce an electrochemically measurable species that can be detected by the electrodes. It is contemplated that other enzymes may be used to react with glucose such as glucose dehydrogenase. If the concentration of another analyte is to be determined, an appropriate enzyme is selected to react with the analyte.

A fluid sample (e.g., blood) may be applied to the fluid-receiving area 128 at or near channel 124. The fluid sample travels through the channel where it then reacts with the at least one reagent. After reacting with the reagent and in conjunction with the plurality of electrodes, the fluid sample produces electrical signals that assist in determining the analyte concentration. The conductive leads carry the electrical signal back toward a second opposing end of the biosensor 100, such as the port-insertion region 126, where the biosensor contacts 122*a*, 122*b* transfer the electrical signals into the meter when the biosensor is inserted into the meter.

As discussed above, a sensor may analyze the analyte in a sample using an electrochemical analysis. It is also contemplated that a sensor may analyze the analyte in a sample using an optical analysis or a combination of optical and electrochemical methods. As discussed above, during electrochemical analyses, an excitation signal is applied to the sample of the biological fluid. The excitation signal may be a potential or current and may be constant, variable, or a combination thereof. The excitation signal may be applied as a single pulse or in multiple pulses, sequences, or cycles. Various electrochemical processes may be used such as amperometry, coulometry, voltammetry, gated amperometry, gated voltammetry, and the like.

Optical test sensor systems may use techniques, such as transmission spectroscopy, diffuse reflectance, spectroscopy, or fluorescence spectroscopy, for measuring the analyte concentration. An indicator-reagent system and an analyte in a sample of body fluid are reacted to produce a chromatic reaction, as the reaction between the reagent and analyte causes the sample to change color. The degree of color change is indicative of the analyte concentration in the body fluid.

An optical test sensor can include auto-calibration information and a sample-receiving area (e.g., fluid-receiving area). The sample-receiving area includes an indicator-reagent system that is adapted to produce a chromatic reaction after being exposed to an analyte in a fluid sample. The reagent may be dried and then mixed with the sample in the sample-receiving area. Alternatively, the reagent may be deposited with the sample or after the sample has been received in the sample-receiving area.

An optical analysis generally measures the amount of light absorbed or generated by a reaction of a chemical indicator with an analyte. An enzyme may be included with the chemical indicator to enhance the reaction kinetics. The light from an optical system may be converted into an electrical signal such as current or potential by a detector.

In light-absorption optical analyses, a chemical indicator produces a reaction product that absorbs light. An incident excitation beam from a light source is directed toward the sample. The incident beam may be reflected back from or transmitted through the sample to a detector or sensor. The detector collects and measures the attenuated incident beam. The amount of light attenuated by the reaction product is an indication of the analyte concentration in the sample.

In light-generated optical analyses, the chemical indicator produces a reaction product that fluoresces or emits light in response to the analyte during the redox reaction. A detector collects and measures the generated light. The amount of light produced by the chemical indicator is an indication of the analyte concentration in the sample.

A biosensor can be made from a variety of materials such as polymeric materials. Non-limiting examples of polymeric materials that may be used to form a base, a lid, and any spacers of a biosensor include polycarbonate, polyethylene terephthalate (PET), polyethylene naphthalate (PEN), polyimide, and combinations thereof. It is contemplated that other materials may be used in forming a biosensor base, lid, and/or spacer.

To form the biosensor, the base, the spacer, and the lid are attached by, for example, an adhesive or heat sealing. When the base, the lid, and/or the spacer are attached, the fluid-receiving area 128 and channel 124 are formed. The fluid-receiving area 128 provides a flow path for introducing the fluid sample into the biosensor.

The exemplary biosensor 100 depicted in FIG. 1 also includes a serial calibration code pattern 130 disposed generally along a first side 112 of the biosensor 100. The serial calibration code pattern 130 includes optically transparent portions (e.g., 132) that allow light waves to be transmitted therethough. The bio sensor 100 further includes a synchronization code pattern 140 disposed generally along a second side 114 of the biosensor 100. The synchronization code pattern 140 also includes optically transparent portions (e.g., 142) that allow light waves to be transmitted therethrough with optically transparent openings being generally evenly spaced along the pattern 140 with optically non-transparent portions in between. While the serial calibration code pattern 130 and the synchronization code pattern 140 are depicted as two parallel strings on two opposing sides 112, 114 of the biosensor 100, it is contemplated that the strings can be offset from each other or even located adjacent to each other with at least some separation or barrier between the respective patterns 130, 140 as long as the synchronization code pattern 140 corresponds to the serial calibration code pattern 130. The correspondence between these two patterns 130, 140 provides synchronization of the serial calibration code pattern 130 during insertion of the port-insertion region 126 into a receiving port of an analyte meter, which will be discussed in more detail below including in the context of FIGS. 2-6.

The benefit of combining a serial calibration code pattern with a corresponding synchronization code pattern on a sensor is that a large number of different calibration codes can be encoded onto the sensor within a limited area allowing the test sensor size to remain relatively unchanged while still allowing the sampling of a biological fluid and insertion of the sensor into an analyte measurement meter. For example, the non-limiting embodiment of bio sensor 100 and variations thereof allows for anywhere from hundreds to thousands of calibration codes within the very limited space of the bio sensor 100 through the use of the optically transparent coding patterns that can be read with an optical pattern reader associated with the analyte measurement meter. The illustrated sixteen optically transparent synchronization openings along pattern 140, allow up to 65,536 (i.e., 2 to the $16^{th}$ power assuming the meter is operating in binary) different calibration codes can be available for applying a correction to an analyte concentration determination. If only half the synchronization openings were used, up to 256 (i.e., 2 to the $8^{th}$ power assuming the meter is operating in binary) different calibration codes would be available. Similarly, if only a quarter of the synchronization openings were used, up to 16 (i.e., 2 to the $4^{th}$ power assuming the meter is operating in binary) different calibration codes would be available. Thus, the number of calibration codes that are available is exponentially related to the number of synchronization openings disposed on the sensor. While providing what could be nearly an unlimited number of calibration codes using serial calibration coding methods, the addition of synchronization coding allows this to be done within the same amount of surface area on a sensor strip that would normally be occupied by parallel coding methods. A significant increase in the number of available calibration codes increases the accuracy and precision of analyte concentration measurements.

A biosensor can include at least a portion of the serial calibration code pattern or at least a portion of the synchronization code pattern being formed by apertures or holes (e.g., 132, 142) in the test sensor material. The patterns may also be formed using optically transparent materials separated by non-transparent portions. For the synchronization code patterns, the apertures or optically transparent opening are arranged in an evenly spaced manner in serial fashion as illustrated, for example, in synchronization code pattern 140 where the synchronization code pattern has evenly distributed openings each separated by evenly distributed optically non-transparent material. The evenly spaced synchronization code patterns act as clock pulses that are synchronized with the calibration coding pattern. The calibration code patterns can also include apertures or optically transparent materials arranged in a serial fashion on the sensor, but may not be evenly spaced and may include a series of larger apertures or optically transparent openings separated by non-transparent portions to create the pattern associated with a calibration code. The patterns can be read using an optical pattern reader. In certain aspects, the serial calibration and synchronization code patterns each have a certain length that is determined by the combination of the optically non-transparent portions and the optically transparent openings that in combination comprise the calibration or synchronization pattern. In some aspects, depending on how the two patterns correspond to each other for synchronization purposes, the synchronization code pattern on the sensor may be approximately the same length as the serial calibration code pattern.

As illustrated in FIG. 1, the serial calibration code pattern 130 can be disposed on the sensor parallel to the synchronization code pattern 140. In FIG. 1, the patterns 130, 140 are disposed on opposing sides 112, 114 of the test sensor. The serial calibration code pattern is disposed on the sensor parallel to and physically separated from the synchronization code pattern by an optically non-transparent portion of the sensor. However, it is contemplated that the code patterns 130, 140 can be disposed at other locations on the test sensor so long at the synchronization code pattern corresponds to the calibration code pattern.

In some aspects, it is contemplated that a test sensor can include a port-insertion region having a first side and an opposing second side. The serial calibration code pattern can be oriented parallel to and along the first side (e.g., an edge of the sensor), and the synchronization code pattern can be oriented parallel to and along the second side (e.g., another edge of the sensor). In certain aspects, the serial calibration code pattern and the synchronization code pattern each include apertures disposed in the strip along the first side and the second side. Each of the apertures of the code patterns may be generally rectangular with all the sides of the apertures (or in some instances less than all the sides e.g., only three sides of the apertures) being defined by the test sensor.

The surface area of the test sensor that is occupied by calibration and synchronization code patterns, while still providing a large number of calibration codes, can be minimized by applying the features described by the present disclosure. For a configuration that provides for up to approximately 65,536 calibration codes, the serial calibration code pattern in some aspects occupies less than 0.04 square inches of a top surface area of the sensor. In some aspects, the serial calibration code pattern occupies less than 0.02 square inches of a top surface area of the sensor. In some aspects, the synchronization code pattern occupies less than 0.04 square inches of a top surface area of the sensor. In some aspects, the synchronization code pattern occupies less than 0.02 square inches of a top surface area of the sensor. In some aspects, the serial calibration code pattern and the synchronization code pattern together occupy less than 0.06 square inches of a top surface area of the sensor. In certain aspects, the serial calibration code pattern and the synchronization code pattern together occupy less than 0.03 square inches of a top surface area of the sensor.

Referring now to FIG. 2, an exemplary side view of the biosensor 100 is depicted along with an artificial light source 160 and light sensor 170 that may be part of an optical pattern reader used to obtain data encoded onto the biosensor 100. In some aspects, it is contemplated that the artificial light source 160 may be a light-emitting diode (LED) or another light source that is known for optical readers in the field of analyte concentration testing. It is contemplated that the light sensor 170 can be a photosensor, an array of light detectors, or another light-sensitive sensor that is known for optical readers in the field of analyte concentration testing.

The test sensor can include a plurality of apertures (e.g., 132, 142) that form the coding patterns. The apertures (e.g., 142) are depicted as clear (unhatched) areas in the side view of FIG. 2. The synchronization code pattern 140 illustrate in FIG. 1 and the cross-sectional view illustrated in FIG. 2 shows a plurality of synchronization code apertures where each of the apertures are evenly spaced and correspond to the calibration code pattern (e.g., 130) illustrated in FIG. 1. The correspondence between the two patterns is illustrated and described in more detail with respect to FIG. 6. One non-limiting example of a calibration code pattern 130 is shown in FIG. 1 with less than all of the potential apertures that could be coded onto the sensor. The selection of which apertures to form for the calibration code pattern determines the calibration code conveyed to the meter or instrument, which is associated with sensor-specific calibration information.

The apertures 132, 142 may be formed by cutting or punching of a test sensor. The cutting or punching may be performed by lasers, mechanical punching, die cutting or by using water jets. The shape of the apertures 132, 142 is shown as being a thin generally rectangular slit. Other shapes are contemplated by the present disclosure includes shapes different from the generally rectangular shapes, such as those depicted in FIGS. 1-9.

It is contemplated that a plurality of optically transparent openings (e.g., 132, 142), such as an aperture, are combined to form the respective coding patterns. The optically transparent openings can include an aperture extending entirely through a sensor (e.g., 100), a transparent opening formed from an optically transparent material extending through the sensor, or through a combination apertures partially extending through a sensor and a remaining portion of optically transparent material. An optically transparent opening allows light to be transmitted through and detected on the opposing side of the sensor. Non-limiting examples of optically clear or translucent material that may be used include "white" or clear polyethylene terephthalate (PET), "white" or clear polycarbonate, or "white" or clear glycol-modified PET (PETG). Alternatively, an optically clear substrate may be covered with an opaque coating that is then selectively removed to form optically transparent openings. Examples of such opaque coatings are metals, such as aluminum, gold or copper formed by vacuum deposition, sputtering or plating, and carbon, which may be coated or printed.

The light source 160 illustrated in FIG. 2 can be part of an optical pattern read device that includes one or more of the light sources and a plurality of light sensors (e.g., 170). The artificial light source 160 can include a light-emitting diode (or other type of light) 162 that may be covered by a light mask 164 shaped to direct light generated by the LED through a narrow mask opening 168, and into the optically transparent openings defining the codes, such that a light beam 180 from the light source is received by the light sensor 170. The light sensor 170 can include a photosensor 172 or other light sensing element that may be covered by a sensor mask 174 that may further include a narrow light receiving opening 178. The use of masks 168, 178 can be beneficial for directing the light beam 180 directly into an optically transparent code opening and also for minimizing or preventing the receipt of any errant light from another light source that might give a false positive detection by the light sensor 170. The masks can also be configured, at least for the light source, so that the emitted light beam is narrower than the smallest dimension of the optically transparent openings (e.g., apertures). While FIG. 2 illustrates a cross-section through a synchronization code pattern, the light source and light sensor features and the aspects of transmitting light through an optically transparent opening (e.g., 132, 142) is generally the same for both the synchronization and calibration code patterns.

The artificial light source 160 and light sensor 170 may be part of a biosensor system for determining an analyte concentration in a biological fluid. The biosensor system may include a measurement device including a processing unit connected to an optical pattern read device. The optical pattern read device can include one or more light sources and a plurality of light sensors. A sensor strip, such as sensor 100 illustrated in FIGS. 1 and 2, includes sequential data coding patterns including first optically transparent openings (e.g., 132, 142) and separate corresponding synchronization coding patterns including second optically transparent openings. The one or more light sources (e.g., 160) can be configured to transmit light waves through the first and second optically transparent openings (e.g., 142). The one or more light sources are at least partially positioned on a first side of the first and second optically transparent openings. One of the plurality of light sensors (e.g., 170) is positioned on an opposite side of the first optically transparent openings (e.g., 132) and another of the plurality of light sensors is positioned on an opposite side of the second optically transparent openings (e.g., 142). The light sensors (e.g., 170) are configured to receive transmitted light waves from the one or more light sources. The light sensors generate a sequence of pulses in response to the light waves or light beams being transmitted through the optically transparent openings associated with the sequential data coding patterns and the synchronization coding patterns.

In some aspects, the one or more artificial light sources may be just a single light source (e.g., 160). A plurality of light guides (not shown) can be employed to receive light from an LED light (e.g., 162) and redirect the light beam from the light to the optically transparent openings. One light guide can direct the light beam to the calibration code pattern and another light guide can direct the split light beam to the synchronization code pattern. The light beams are directed by total internal reflection within the plurality of light guides. It is also contemplated that the light beams may further be redirected by reflecting surfaces present in the light guide(s). The plurality of light guides can further be configured to emit light beams narrower than the smallest dimension of the optically transparent openings.

In some aspects, the one or more light sources may include two light sources (e.g., LEDs). One light may be positioned to transmit light waves through first optically transparent openings and into the first light sensor that may be associated with the serial calibration code patterns. The other light may be positioned to transmit a light beam through the second optically transparent openings and into the second light sensor associated with the serial synchronization code patterns.

Turning now to FIGS. 3 and 4, a top view and a side view are illustrated of a sensor strip 300 with serial optical coding that is inserted into a sensor interface 390 including an optical pattern read device 380. The sensor 300 includes a port-insertion region 326 and a fluid-receiving area 328. The port-insertion region 326 of the sensor 300 can be inserted into the sensor interface 390 as illustrated in FIGS. 3 and 4. As the sensor 300 is inserted into the sensor interface 390, sensor detection contacts 394a, 394b will complete a circuit as contact 394b is pushed up and touches contact 394a to complete the detection circuit. A first end 396 of a sensor detection contact 394b can be positioned at the portion of the sensor interface where the sensor is first inserted and before the sensor is placed below the optical pattern reader. The completion of the circuit between contacts 394a and 394b causes a signal to be received in a controller or other processing unit that initiates instructions for the optical pattern read device 380 to begin transmitting light from light source(s) 360 to light sensor(s) 370 as the sensor 300 is inserted into the sensor interface. The transmitting and receiving of light is configured to occur as the calibration code patterns and corresponding synchronization code patterns pass through the light beam created by the light source-light sensor arrangement.

As the sensor 300 is inserted into the sensor interface, the code pattern is read by the optical pattern read device so that a calibration code can be determined for use in an equation for determining an analyte concentration for a fluid sample received in the fluid-receiving area. The sensor 300 includes contacts 312a, 312b that complete a circuit with sensor interface contacts 392a, 392b, which are used to electrochemically determine a value associated with an analyte concentration for the received fluid sample in the fluid-receiving area 328. The sensor interface may be associated with or be a part of a measurement device in a biosensor system for determining an analyte concentration in a biological fluid. For example, the sensor interface may be a part of a blood glucose meter or another analyte meter and comprise all or a portion of a sensor receiving area of such meters.

In some aspects, it is contemplated that a sensor strip detection system detects a sensor strip being inserted into a port of a measurement device, such as an analyte meter. The sensor strip is detected by the detection system immediately prior to commencing the optical reading of the sequential or serial data coding patterns and the synchronization coding patterns.

An optical pattern read device (e.g., 380) including light sources (e.g., 160, 360) and light sensors (e.g., 170, 370) are configured to measure optical transmissions through an array of fine optically transparent openings for the serial calibration and synchronization codes disposed in a biosensor. In some aspects, and as illustrated for example in FIGS. 2 and 4, the light sensor (or light receiver) is disposed on the opposite side of a sensor from where the light beam generated by the artificial light source first enters the optically transparent opening in the sensor. It is contemplated that similar arrangements of the artificial light source and light sensor are applicable for reading both the serial synchronization code patterns and the serial calibration code patterns on a sensor. As illustrated by the non-limiting embodiment of FIGS. 3 and 4, as the sensor is moving or inserted into a port or sensor interface, the light sensor (e.g., 370) generates a sequence of pulses in response to the receipt or lack thereof of artificial light beams transmitted from the light source. The receipt of an artificial light beam by the sensor occurs in when an optically transparent opening (e.g., aperture associated with coding) is present between the light source and receiver. The lack of receipt of artificial light occurs when an optically non-transparent portion is disposed on the sensor, for example between two optically transparent openings, and blocks a light beam from being received by the light sensor.

It is contemplated that the optical pattern read device may include a microcontroller (or be associated with a microcontroller or another processing unit) that processes the data pulses to determine the calibration code for the test sensor. The received calibration data pulses correspond with the synchronization pulses to allow for a large number of calibration codes to be available in a limited space. For example, while a sensor strip is being inserted into the measurement device, light waves or light beams may be transmitted by both the first and second light sources and received by a first light sensor associated with serial or sequential calibration code patterns and a second light sensor associated with serial or sequential synchronization code patterns. The light waves or light beam received by the second light sensor provides synchronization for the light waves received by the first light sensor.

Figure 5:
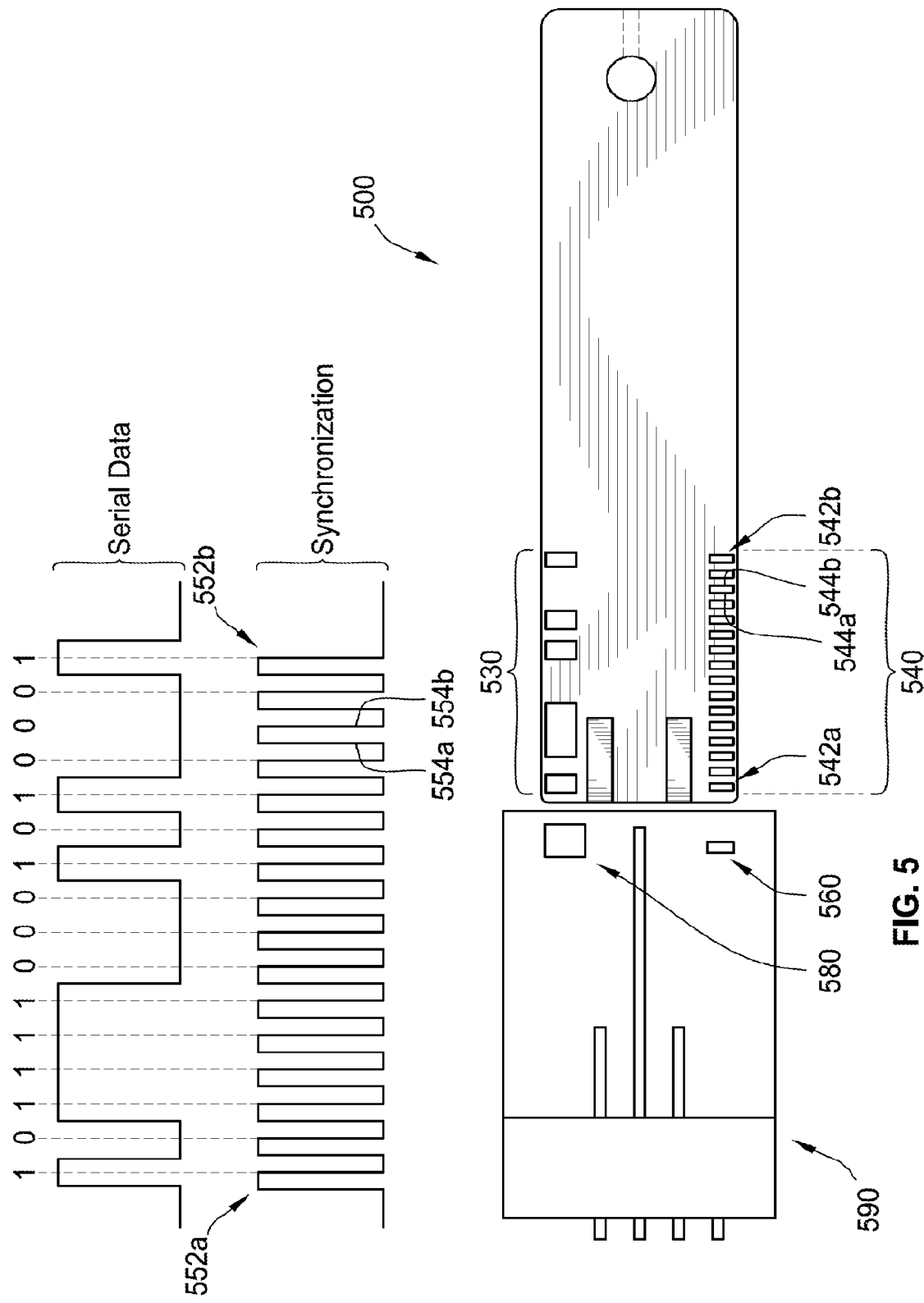
FIG. 5 illustrates a sensor strip adjacent to a sensor interface and optical pattern read device along with code and synchronization signals generated by the insertion of the sensor strip into the sensor interface.
Figure 6:
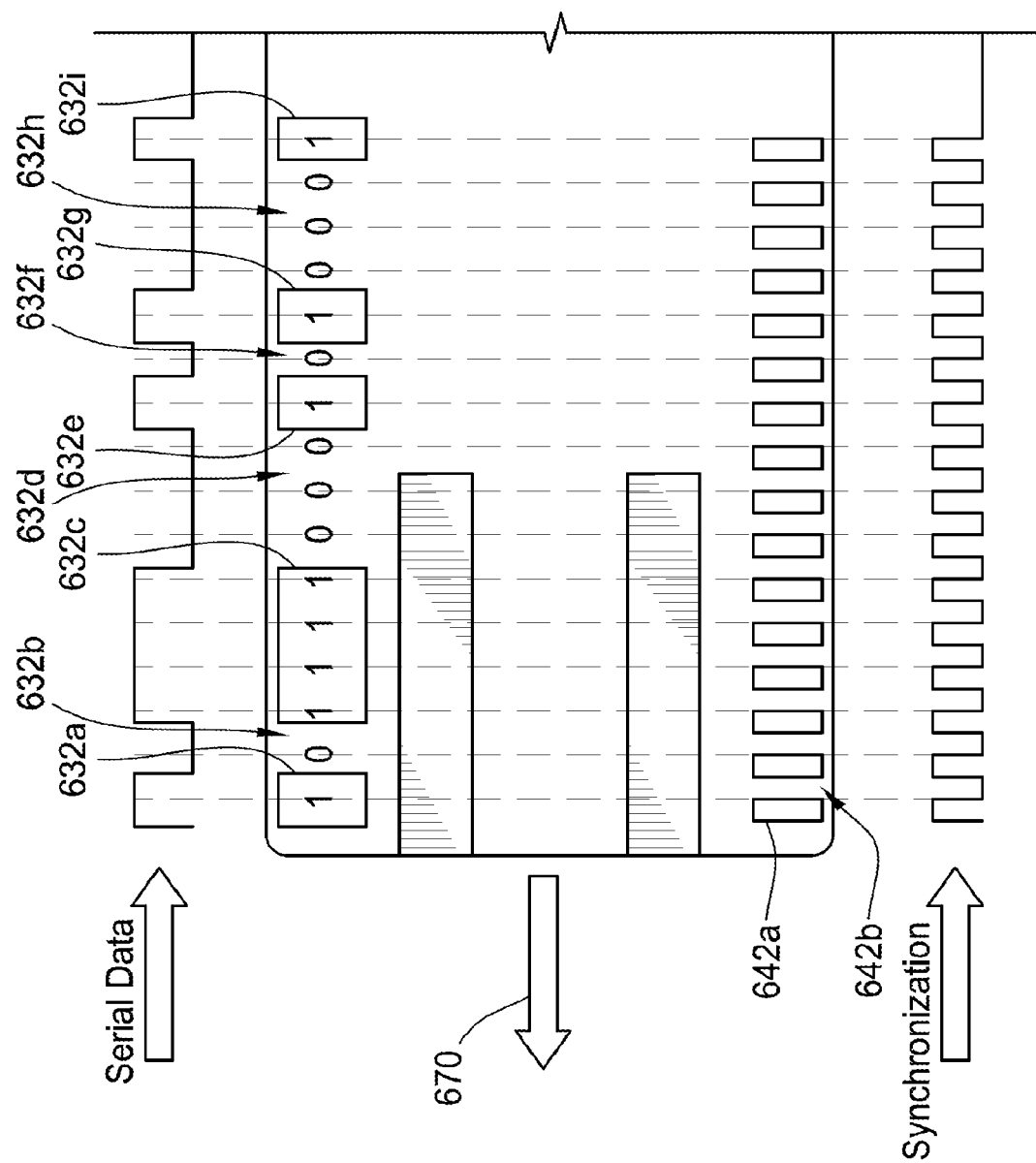
FIG. 6 illustrates another aspect of the code and synchronization signals generated by the insertion of the sensor strip into the sensor interface.

Turning now to FIGS. 5 and 6, a non-limiting top view of an exemplary sensor strip 500 is depicted adjacent to a sensor interface 590 having optical read features such as a calibration light source 580 and a synchronization light source 560, each having respective sensors (not shown) opposite the light source with a small gap therebetween to allow for passage of the sensor, and more specifically, passage of the respective exemplary serial calibration code pattern 530 and exemplary serial synchronization code pattern 540. The synchronization code pattern 540 includes a first optically transparent opening 542a followed by a series of additional evenly spaced optically transparent openings and ending with a last optically transparent opening 542b. Each opening in the synchronization code pattern includes a front side (e.g., 544a) and an end side (e.g., 544b) corresponding to the beginning and the end of the optically transparent opening identifiable by an optical pattern reader (e.g., including one or more light source and light sensor combinations).

FIG. 5 also illustrates a non-limiting example of the type of "Serial Data" signals generated by the light sensor associated with the serial calibration code pattern 530 and the corresponding "Synchronization" signals generated by the light sensor associated with the serial synchronization code pattern 540. A first pulse signal 552a of the synchronization code pattern corresponds to exemplary first opening 542a and a last pulse signal 552b corresponds to exemplary last opening 542b. An initial spike (e.g., 554a) of a pulse corresponds to the optical pattern reader identifying the front side (e.g., 544a) of a code pattern opening and the end spike (e.g., 554b) corresponds to the optical reader identifying the end side (544b) of the same code pattern. More details of non-limiting exemplary aspects regarding the synchronization and calibrations code patterns and the correspondence between the two is depicted in FIG. 6 along with the determination of the binary data generated from the code patterns.

As illustrated in FIGS. 5 and 6, the sequential or serial data coding patterns (e.g., 530) and the synchronization coding patterns (e.g., 540) cause a series of corresponding positive (e.g., "1") and negative (e.g., "0") code signals to be generated by the optical read head device. These code signals are received by the processing unit and processed in a binary form (e.g., "0" and "1"). The code signals are received while the sensor strip is inserted into the measurement device. The measurement device (e.g., an analyte meter) and sensor strip are configured to implement an analyte analysis having at least one correlation equation associated with a calibration code determined from the sequential data coding patterns. A processing unit is configured to calibrate the at least one correlation equation in response to the generated code signals received from the optical pattern read device. The processing unit is further configured to determine an analyte concentration responsive to the at least one calibrated correlation equation.

In it contemplated that the synchronization code pattern can include anywhere from between about eight to about sixteen or more sequential and evenly spaced optically transparent openings disposed on a test sensor. Each of the evenly spaced synchronization code openings (e.g., 540) corresponds to one of a series of sequential optically transparent openings and non-transparent positions that comprise the calibration code pattern (e.g., 530) on the same test sensor.

Referring now to FIG. 6, a portion of a test sensor that includes the port-insertion region is depicted, similar to the sensor illustrated in FIG. 5 (including similar serial data and synchronization codings). This non-limiting example of a coded test sensor includes a series of optically transparent openings 632a, 632c, 632e, 632g, 632i that are respectively separated by optically non-transparent portions 632b, 632d, 632f, 632h that are disposed on the test sensor. The test sensor can be inserted into a port or opening of an analyte meter in direction 670. As the test sensor is inserted into the port, signals are generated by a light sensor of an optical pattern read device. The generated signal is depicted by the "Serial Data" illustrated in FIG. 6. As calibration code opening 632a passes between a light source and light sensor, as described, for example in FIG. 2, a positive signal is generated by the light sensor in response to receiving the light beam transmitted from the light source. The positive signal may be interpreted in binary form as a "1" by a processor (e.g., microcontroller) associated with (e.g., connected to) the light sensor or the optical pattern read device. Next, an optically non-transparent portion 632b passes between the light source and light sensor generating a negative signal by the light sensor as a light beam is not received from the light source. The negative signal may be interpreted in binary form as a "0" by the processor.

Near simultaneous to the generation of the serial data from the serial calibration code pattern, a corresponding synchronization code pattern is being read and a light sensor generates signals (e.g., "Synchronization") that act as a clocking system for respective positions of the corresponding optically transparent openings and optically non-transparent portions of the calibration coding pattern. For example, optically transparent synchronization code opening 642a is "clocked" to correspond to optically transparent calibration code opening 632a. Optically non-transparent synchronization portion 642b is "clocked" to correspond to optically non-transparent calibration portion 632b. In some aspects, the synchronization code pattern comprises a series of similarly sized optically transparent openings that are evenly spaced in series with a similarly sized gap of optically non-transparent material the optically transparent openings.

Referring again to the calibration code openings for test sensor in FIG. 6, after the optically non-transparent portion 632b causes a generation of a negative signal, a series of calibration positions that form optically transparent opening 632c causes a series of positive signals to be generated by the optical pattern read device in correspondence with clocking or synchronization signals generated by the synchronization light sensor for the optically transparent synchronization code openings. In the non-limiting example of opening 632c, the generated positive signals are interpreted by the processor in a binary form of "1-1-1-1". This is followed by a series of calibration positions that form another optically non-transparent portion 632d that causes a series of negative signals to be generated by the optical pattern read device in correspondence with clocking or synchronization signals generated by the synchronization light sensor for the synchronization code opening that correspond with the series of calibration positions associated with portion 632d. The generated negative signals are interpreted by the processor in a binary form of "0-0-0". Similar generation of signals and subsequent processor interpretations occur for openings 632e, 632g 632i and portions 632f, 632h in correspondence with their respective synchronization code openings.

The number of synchronization code openings determines the number of possible calibration codes for a test sensor. For example, FIG. 6 includes sixteen evenly spaced synchronization code openings (e.g., 642a) that allow for a pattern including sixteen calibration code positions that can be either a "1" or a "0" depending on if a positive a negative signal is generated for a particular calibration position. This means that the maximum number of possible calibration codes for this non-limiting embodiment is 65,536 codes (i.e., 216). More or fewer calibration codes are possible by adding or removing the number of synchronization code openings, and thus, adding or removing the number of calibration code positions. The number of possible calibration codes increases and decrease exponentially (by a factor of two in the exemplary binary aspect illustrated for the present disclosure) for each added or removed synchronization opening. Furthermore, while FIGS. 5 and 6 depict a generated calibration signal corresponding to a binary calibration code of "1011110001010001", this is just one of 65536 calibration codes (e.g., ranging from 0000000000000000 to 1111111111111111) that can be generated by changing the serial pattern of optically transparent calibration openings and optically non-transparent calibration portions comprising the calibration coding pattern on a test sensor.

Turning now to FIGS. 7 and 8, two non-limiting exemplary aspects of test sensors 700, 800 are depicted. Test sensors 700, 800 include optically transparent serial data coding patterns created by punching apertures (e.g., 732, 832) into the sensor strips. Test sensor 700, 800 also includes optically transparent synchronization coding patterns also created by punching apertures (e.g., 742, 842) into the sensor strip. The apertures (e.g., 732, 832) for the serial data coding can be of varying sizes that depend on the calibration code for a sensor and whether a given position along the calibration coding is intended to generate a positive or negative signal. Thus, if a given aperture is coded to provide a series of positive signals (e.g., "1-1-1"), the aperture will be wider than an aperture that is coded to only provide a single positive signal (e.g., "1") preceding and followed by one or more portions intended to generate a negative signal (e.g., "0"). The apertures (e.g., 742, 842) for the synchronization coding patterns are generally the same size and are evenly spaced in a serial fashion. The apertures 732, 742 in sensor 700 are generally rectangular and are disposed entirely within the sensor 700 such that sensor material forms a perimeter around each aperture. The apertures 832, 842 in sensor 800 are generally square or rectangular and are disposed along the perimeter of the sensor 800 such that sensor material only forms a partial perimeter around each aperture. While generally rectangular shapes are depicted for the apertures 732, 742, 832, 842, it is contemplated that other shapes can be used as would be understood in the field of optical pattern readers.

Figure 9:
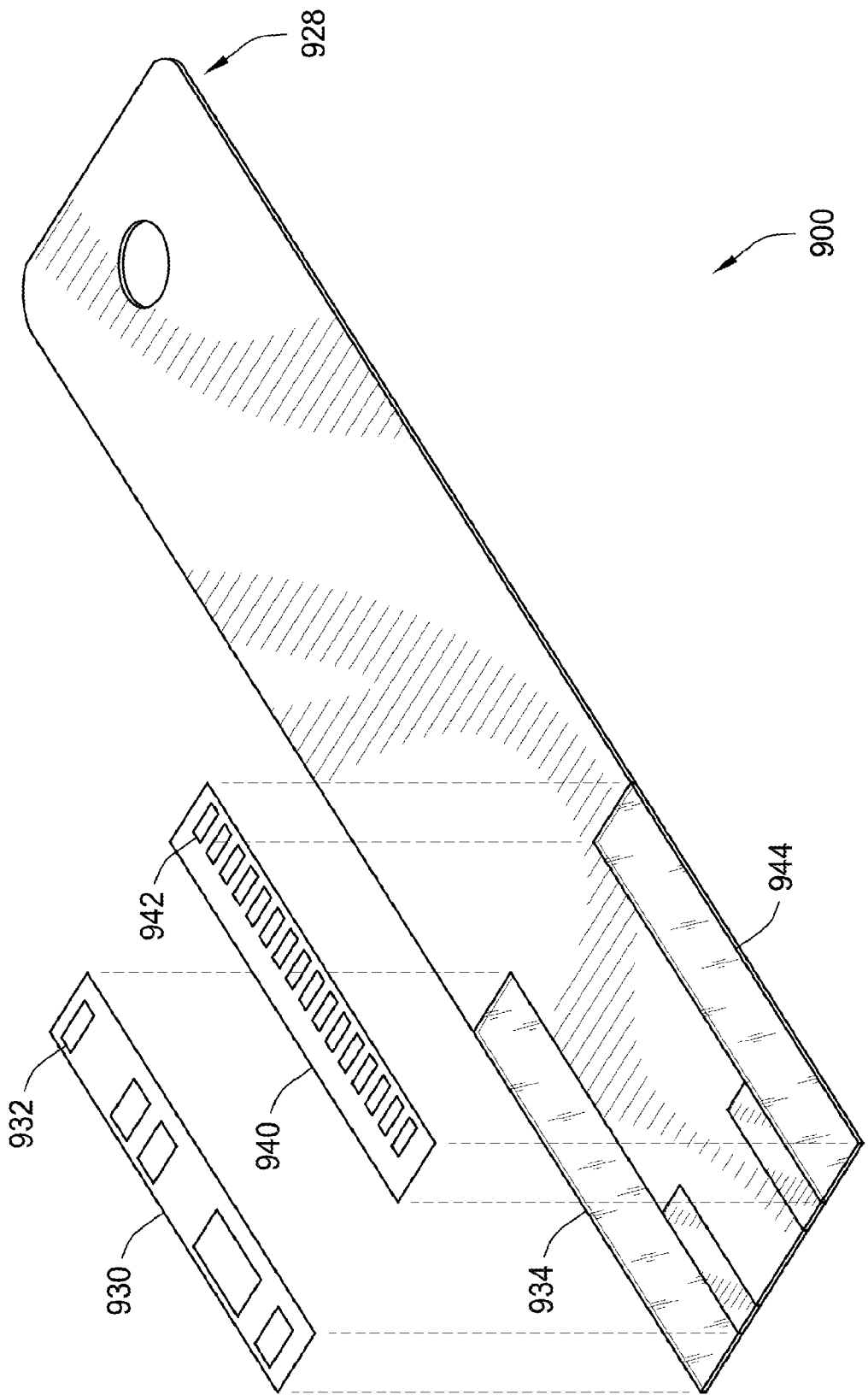
FIG. 9 illustrates a sensor strip including optically transparent serial data coding patterns and synchronization coding patterns created by placing printed coding patterns on a transparent area of the sensor strip according to one embodiment.

Turning now to FIG. 9, a sensor strip 900 is depicted including optically transparent serial data coding patterns and synchronization coding patterns created by placing printed coding patterns 930, 940 on a transparent area 934, 944 of the sensor strip. Similar to other sensors described above, the sensor strip 900 may include a port-insertion region 926 and a fluid-receiving area 928. The port-insertion region 926 can include two sections 934, 944 of optically transparent material. A first section 934 of optically transparent material can have a calibration overlay 930 adhered to or printed onto the optical transparent layer 934 to form a pattern for the serial calibration coding for the sensor strip 900. The calibration overlay 930 can have a plurality of data openings (e.g., 932) printed, punched, or otherwise cut into the overlay. Similarly, a second section 944 of optically transparent material can have a synchronization overlay 940 adhered to or printed onto the optical transparent layer 944 to form a pattern for the serial synchronization coding for the sensor strip 900. The synchronization overlay 940 can have a plurality of synchronization openings (e.g., 942) printed, punched, or otherwise cut into the overlay.

Figure 10:
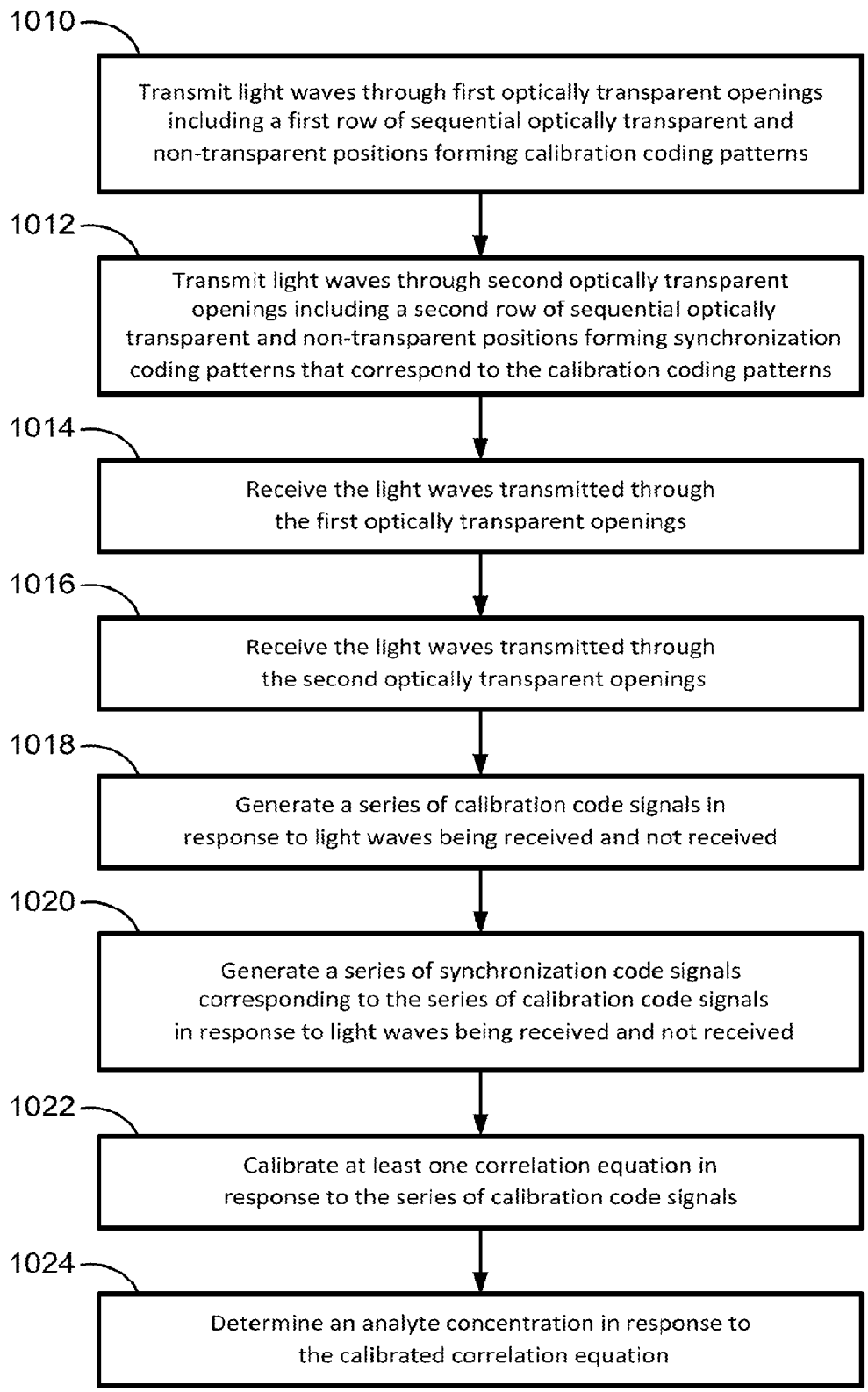
FIG. 10 is a flowchart of an exemplary method for calibrating an analysis of an analyte in a fluid sample according to certain embodiments.

Turning now to FIG. 10, a flowchart for an exemplary method for calibrating an analysis of an analyte in a biological fluid is illustrated. The actions identified in the flowchart and described below correspond to instructions that may be stored in a memory and executed by one or more processing units within or connected to a fluid analyte meter, such as a blood glucose meter or other types of fluid analyte meters including portable or stationary units. First, at step 1010, the method includes the act of transmitting light waves through first optically transparent openings in a test sensor that includes a first row of sequential optically transparent and non-transparent positions forming calibration coding patterns. Next, at step 1012, nearly simultaneous to the act in step 1010, the act of transmitting light waves through second optically transparent openings in the test sensor is implemented. The transparent openings include a second row of sequential optically transparent and non-transparent positions on the test sensor that form synchronization coding patterns that correspond to the calibration coding patterns. Then, at step 1014, the light waves transmitted through the first optically transparent openings are received by a first light sensor, and at step 1016, light waves transmitted through the second optically transparent openings are received by a second light sensor. Next, at step 1018, the act of generating a series of calibration code signals is implemented in response to light waves being received and not received by the first light sensor. The light waves are received and not received in response to the optically transparent and non-transparent positions passing the first light sensor during the insertion of the test sensor into the analyte measuring device. Then, at step 1020, nearly simultaneous to the act in step 1018, the act of generating a series of synchronization code signals is implemented in response to light waves being received and not received by the second light sensor. The light waves are received and not received in response to the second row of sequential optically transparent and non-transparent positions passing the second light sensor during the insertion of the test sensor into the analyte measuring device. The series of synchronization code signals correspond to the series of calibration code signals. Next, at step 1022, the act of calibrating at least one correlation equation is implemented by one or more processing units in response to the generated series of calibration code signals. Finally, at step 1024, the act of determining an analyte concentration is implemented by at least one of the one or more processing units based on the at least one calibrated correlation equation. The analyte concentration determination further includes reacting the analyte in an electrochemical reaction that produces an output signal. The analyte concentration is then calculated using the at least one calibrated correlation equation and the produced output signal.

In some aspects, it is contemplated that a method for calibrating an analysis of an analyte in a biological fluid can further include detecting the insertion of the test sensor into an insertion port of an analyte meter. The detecting can occur immediately prior to transmitting of light waves or a light beam through optically transparent openings and non-transparent positions forming the calibration coding patterns and the synchronization coding patterns. It is further contemplated that calibration coding patterns have a length where the synchronization coding patterns are about the same length as the calibration coding patterns. In some aspects, the second row of sequential optically transparent and non-transparent positions are evenly spaced. The calibration coding patterns may be disposed on the test sensor parallel to and physically separated from the synchronization coding patterns by an optically non-transparent portion of the strip.

While the invention has been described with reference to details of the illustrated embodiments, these details are not intended to limit the scope of the invention as defined in the appended claims. For example, although the illustrated embodiments are generally directed to a synchronization code pattern that includes sixteen positions or optically transparent openings, coding patterns with more or fewer optically transparent openings, along with different arrangements, are contemplated to provide a clocking mechanism for the calibration code patterns. Furthermore, different types of optically transparent openings are contemplated including hybrids of both transparent material and partial apertures in the test sensor material. In addition, it should be noted that the cross-section and other geometrical aspects of the sensor interface, light sources, light sensors, and sensors used herein may be other shapes such as circular, square, hexagonal, octagonal, other polygonal shapes, or oval. The non-electrical components of the illustrated embodiments are typically made of a polymeric material. Non-limiting examples of polymeric materials that may be used in forming devices and strips include polycarbonate, ABS, nylon, polypropylene, or combinations thereof. It is contemplated that the fluid analyte systems can also be made using non-polymeric materials. The disclosed embodiments and obvious variations thereof are contemplated as falling within the spirit and scope of the claimed invention.

Alternative Aspects

According to an alternative aspect A, a test sensor for determining an analyte concentration in a biological fluid includes a strip including a fluid-receiving area and a port-insertion region; a first row of optically transparent and non-transparent positions forming a calibration code pattern disposed within a first area of the port-insertion region; and a second row of optically transparent and non-transparent positions forming a synchronization code pattern disposed within a second area of the port-insertion region, the second area being different from the first area, wherein the synchronization code pattern corresponds to the calibration code pattern such that the synchronization code pattern provides synchronization of the calibration code pattern during insertion of the port-insertion region into a receiving port of an analyte meter.

According to an alternative aspect B, the test sensor of the preceding aspect further includes that the test sensor is an electrochemical test sensor, the strip further including one or more electrical contacts at least partially disposed within the port-insertion region, the electrical contacts configured to align and electrically connect with sensor contacts of the analyte meter upon insertion of the port-insertion region into the receiving port.

According to an alternative aspect C, the test sensor of any one of preceding aspects A or B further includes that the calibration code pattern and the synchronization code pattern include at least one aperture in the strip, the at least one aperture defining one or more of the optically transparent positions.

According to an alternative aspect D, the test sensor of any one of preceding aspects A to C further includes that the calibration code pattern has a length, the synchronization code pattern having the same length as the calibration code pattern.

According to an alternative aspect E, the test sensor of any one of preceding aspects A to D further includes that the positions forming the calibration code pattern are linearly disposed on the strip parallel to the synchronization code pattern.

According to an alternative aspect F, the test sensor of any one of preceding aspects A to E further includes that the calibration code pattern is disposed on the strip parallel to and physically separated from the synchronization code pattern by an optically non-transparent portion of the strip.

According to an alternative aspect G, the test sensor of any one of preceding aspects A to F further includes that the port-insertion region includes a first edge and an opposing second edge, the calibration code pattern being oriented parallel to and along the first edge, the synchronization code pattern being oriented parallel to and along the second edge.

According to an alternative aspect H, the test sensor of any one of preceding aspects A to G further includes that the calibration code pattern and the synchronization code pattern each include apertures disposed in the strip along the first edge and the second edge, each of the apertures of the code patterns being generally rectangular with only three sides of the apertures being defined by the strip.

According to an alternative aspect I, the test sensor of any one of preceding aspects A to H further includes that the test sensor includes a reagent, the reagent including glucose oxidase and/or glucose dehydrogenase.

According to an alternative aspect J, the test sensor of any one of preceding aspects A to I further includes that the calibration code pattern includes between about eight and about sixteen optically transparent first openings and the synchronization code pattern includes between about eight and about sixteen optically transparent second openings.

According to an alternative aspect K, the test sensor of any one of preceding aspects A to J further includes that the calibration code pattern occupies less than 0.04 square inches of a top surface of the strip.

According to an alternative aspect L, the test sensor of any one of preceding aspects A to J further includes that the calibration code pattern occupies less than 0.02 square inches of a top surface of the strip.

According to an alternative aspect M, the test sensor of any one of preceding aspects A to L further includes that the synchronization code pattern occupies less than 0.04 square inches of a top surface of the strip.

According to an alternative aspect N, the test sensor of any one of preceding aspects A to L further includes that the synchronization code pattern occupies less than 0.02 square inches of a top surface of the strip.

According to an alternative aspect O, the test sensor of any one of preceding aspects A to N further includes that the calibration code pattern and the synchronization code pattern together occupy less than 0.06 square inches of a top surface of the strip.

According to an alternative aspect P, the test sensor of any one of preceding aspects A to N further includes that the calibration code pattern and the synchronization code pattern together occupy less than 0.03 square inches of a top surface of the strip.

According to an alternative aspect Q, the test sensor of any one of preceding aspects A to P further includes that the test sensor is an optical test sensor.

According to an alternative aspect R, a test sensor for determining an analyte concentration in a biological fluid includes a strip including a fluid-receiving area and a port-insertion region, one or more electrical contacts at least partially disposed within the port-insertion region, the electrical contacts configured to align and electrically connect with sensor contacts of an analyte meter upon insertion of the port-insertion region into a receiving port of the analyte meter; a serial calibration code pattern disposed within a first area of the port-insertion region, the serial calibration code pattern including first optically transparent portions allowing light waves to be transmitted therethrough; and a synchronization code pattern disposed within a second area of the port-insertion region, the second area being different from the first area, the synchronization code pattern including second optically transparent portions allowing light waves to be transmitted therethrough, wherein the synchronization code pattern corresponds to the serial calibration code pattern such that the synchronization code pattern provides synchronization of the serial calibration code pattern during insertion of the port-insertion region into the receiving port of the analyte meter.

According to an alternative aspect S, the test sensor of the preceding aspect further includes that the serial calibration code pattern is disposed on the strip parallel to the synchronization code pattern.

According to an alternative aspect T, the test sensor of any one of preceding aspects R or S further includes that at least one of the first optically transparent portions is physically separated from another of the first optically transparent portions of the serial calibration code pattern by an optically non-transparent material.

According to an alternative aspect U, the test sensor of any one of preceding aspects R to T further includes that the synchronization code pattern has evenly distributed serial openings each separated by evenly distributed optically non-transparent material.

According to an alternative aspect V, the test sensor of any one of preceding aspects R to U further includes that the test sensor includes a reagent, the reagent including glucose oxidase or glucose dehydrogenase.

According to an alternative aspect W, the test sensor of any one of preceding aspects R to V further includes that the serial calibration code pattern includes between about eight and about sixteen optically transparent first openings and the synchronization code pattern includes between about eight and about sixteen optically transparent second openings.

According to an alternative aspect X, the test sensor of any one of preceding aspects R to W further includes that the serial calibration code pattern and the synchronization code pattern together occupy less than 0.06 square inches of a top surface of the strip.

According to an alternative aspect Y, the test sensor of any one of preceding aspects R to X further includes that the serial calibration code pattern and the synchronization code pattern together occupy less than 0.03 square inches of a top surface of the strip.

According to an alternative aspect Z, a biosensor system for determining an analyte concentration in a biological fluid includes a measurement device including a processing unit connected to an optical pattern read device, the optical pattern read device including one or more light sources, a first light sensor, and a second light sensor; and a sensor strip including sequential data coding patterns including first optically transparent openings and separate corresponding synchronization coding patterns including second optically transparent openings, wherein the one or more light sources are configured to transmit light waves through the first and second optically transparent openings, the one or more light sources being at least partially positioned on a first side of the first and second optically transparent openings, wherein the first light sensor is positioned on an opposite side of the first optically transparent openings and the second light sensor is positioned on an opposite side of the second optically transparent openings, the first light sensor and the second light sensor configured to receive transmitted light waves from the one or more light sources, wherein the light waves are transmitted by the one or more light sources and received by the first light sensor and the second light sensor while the sensor strip is being inserted into the measurement device such that light waves received by the second light sensor associated with the synchronization coding patterns provide synchronization for the light waves received by the first light sensor associated with the sequential data coding patterns.

According to an alternative aspect AA, the biosensor of the preceding aspect further includes that the sequential data coding patterns and the synchronization coding patterns cause a series of corresponding positive and negative code signals to be generated by the optical pattern read device and received by the processing unit while the sensor strip is inserted into the measurement device, the measurement device and sensor strip being configured to implement an analyte analysis having at least one correlation equation associated with the sequential data coding patterns, the processing unit configured to calibrate the at least one correlation equation in response to the generated code signals received from the optical pattern read device, the processing unit further configured to determine an analyte concentration responsive to the at least one calibrated correlation equation.

According to an alternative aspect AB, the biosensor of any one of preceding aspects Z or AA further includes that the sequential data code patterns include between eight and sixteen sequential first optically transparent openings, and wherein the synchronization coding patterns include between eight and sixteen sequential and evenly spaced second optically transparent openings.

According to an alternative aspect AC, the biosensor of any one of preceding aspects Z to AB further includes that at least a portion of the sequential data coding patterns are apertures in the sensor strip.

According to an alternative aspect AD, the biosensor of any one of preceding aspects Z to AC further includes that at least a portion of the synchronization coding patterns are apertures in the sensor strip.

According to an alternative aspect AE, the biosensor of any one of preceding aspects Z to AD further includes that the sequential data coding patterns are distributed along a length of the sensor strip, the synchronization coding patterns having the same length as the sequential data coding patterns.

According to an alternative aspect AF, the biosensor of any one of preceding aspects Z to AE further includes that the sequential data coding patterns are disposed on the sensor strip parallel to the synchronization coding patterns.

According to an alternative aspect AG, the biosensor of any one of preceding aspects Z to AF further includes that the synchronization coding patterns are evenly distributed optically transparent sequential openings on a surface of the sensor strip such that each adjacent optically transparent synchronization opening is separated by an optically non-transparent material.

According to an alternative aspect AH, the biosensor of any one of preceding aspects Z to AG further includes that the sequential data coding patterns and the synchronization coding patterns are parallel and physically separated by a portion of the surface of the sensor strip along the entire length of the respective coding patterns.

According to an alternative aspect AI, the biosensor of any one of preceding aspects Z to AH further includes that the sensor strip has a first edge and an opposing second edge, the sequential data coding patterns being sequentially positioned along the first edge and the synchronization coding patterns being sequentially positioned along the opposing second edge.

According to an alternative aspect AJ, the biosensor of any one of preceding aspects Z to AI further includes that the sequential data coding patterns and the synchronization coding patterns include one or more apertures in the sensor strip, each coding pattern aperture being rectangular and defined along only three sides by optically non-transparent material of the sensor strip.

According to an alternative aspect AK, the biosensor of any one of preceding aspects Z to AJ further includes that the biosensor includes a reagent, the reagent including glucose oxidase or glucose dehydrogenase.

According to an alternative aspect AL, the biosensor of any one of preceding aspects Z to AK further includes that the one or more light sources includes a single LED light and two light guides for receiving light from the LED light and redirecting the light waves to the first optically transparent openings and the second optically transparent openings, the light waves being directed by total internal reflection within the two light guides, the two light guides being configured to emit light beams narrower than the smallest dimension of the optically transparent openings.

According to an alternative aspect AM, the biosensor of any one of preceding aspects Z to AL further includes that the one or more light sources includes a two LED lights, one LED light being positioned to transmit light waves through the first optically transparent openings and into the first light sensor, the other LED light being positioned to transmit light waves through the second optically transparent openings and into the second light sensor.

According to an alternative aspect AN, the biosensor of any one of preceding aspects Z to AM further includes that each of the one of more light sources includes a mask configured such that the one or more light sources emit a light beam narrower than the smallest dimension of the optically transparent openings.

According to an alternative aspect AO, the biosensor of any one of preceding aspects Z to AN further includes that the light sensors generate a sequence of pulses in response to the light waves being transmitted through the first optically transparent openings associated with the sequential data coding patterns and the second optically transparent openings associated with the synchronization coding patterns.

According to an alternative aspect AP, the biosensor of any one of preceding aspects Z to AO further includes a sensor strip detection system for detecting the sensor strip being inserted into a port of the measurement device, wherein the sensor strip is detected immediately prior to commencing the optical reading of the sequential data coding patterns and the synchronization coding patterns.

According to an alternative aspect AQ, a method for determining an analyte concentration in a biological fluid using a calibrated correlation equation includes the following acts: (a) transmitting light waves through first optically transparent openings in a test sensor including a first row of sequential optically transparent and non-transparent positions forming calibration coding patterns; (b) near simultaneous to act (a), transmitting light waves through second optically transparent openings in the test sensor including a second row of sequential optically transparent and non-transparent positions forming synchronization coding patterns that correspond to the calibration coding patterns; (c) receiving the light waves transmitted through the first optically transparent openings in a first light sensor; (d) receiving the light waves transmitted through the second optically transparent openings in a second light sensor; (e) generating a series of calibration code signals in response to light waves being received and not received by the first light sensor due to the optically transparent and non-transparent positions passing the first light sensor during the insertion of the test sensor into an analyte measuring device; (f) near simultaneous to act (e), generating a series of synchronization code signals in response to light waves being received and not received by the second light sensor due to the optically transparent and non-transparent positions passing the second light sensor during the insertion of the test sensor into the analyte measuring device, the series of synchronization code signals corresponding to the series of calibration code signals; (g) calibrating at least one correlation equation in response to the generating the series of calibration code signals; and (h) determining an analyte concentration based on the at least one calibrated correlation equation, wherein the analyte concentration is determined by reacting the analyte in a reaction that produces an output signal, the analyte concentration being determined using the at least one calibrated correlation equation and the produced output signal.

According to an alternative aspect AR, the method of the preceding aspect further includes detecting the insertion of the test sensor into an insertion port of an analyte meter, the detecting occurring immediately prior to the transmitting of light waves in steps (a) and (b).

According to an alternative aspect AS, the method of any one of preceding aspects AQ or AR further includes that the calibration coding patterns have a length, the synchronization coding patterns having the same length as the calibration coding patterns.

According to an alternative aspect AT, the method of any one of preceding aspects AQ to AS further includes that the second row of sequential optically transparent and non-transparent positions are evenly spaced.

According to an alternative aspect AU, the method of any one of preceding aspects AQ to AT further includes that the calibration coding patterns are disposed on the test sensor parallel to and physically separated from the synchronization coding patterns by an optically non-transparent portion of the strip.

According to an alternative aspect AV, the method of any one of preceding aspects AQ to AU further includes that the test sensor is for determining blood glucose concentration.

According to an alternative aspect AW, the method of any one of preceding aspects AQ to AV further includes that at least a portion of the sequential optically transparent and non-transparent positions are linearly arranged.

According to an alternative aspect AX, the method of any one of preceding aspects AQ to AW further includes that at least a portion of the sequential optically transparent and non-transparent positions are staggered.

According to an alternative aspect AY, the method of any one of preceding aspects AQ to AX further includes that the reaction is an electrochemical reaction and the output signal is an electric signal.

Each of these embodiments and obvious variations thereof is contemplated as falling within the spirit and scope of the claimed invention, which is set forth in the following claims. Moreover, the present concepts expressly include any and all combinations and subcombinations of the preceding elements and aspects.

The invention claimed is:

1. A biosensor for determining an analyte concentration in a biological fluid, the biosensor comprising:
   a strip including a fluid-receiving area and a port-insertion region;
   one or more sensor contacts at least partially disposed in the port-insertion region and configured to allow a transfer of electrical signals during insertion of the port-insertion region into a receiving port of an analyte meter;
   a row of optically transparent and non-transparent positions forming a synchronization code pattern disposed within a first area of the port-insertion region, the first area being different from a second area of the port-insertion region containing a calibration code pattern, the one or more sensor contacts separating the first area and the second area,
   wherein the synchronization code pattern corresponds to the calibration code pattern such that the synchronization code pattern provides synchronization of the calibration code pattern following insertion of the port-insertion region into the receiving port.

2. The biosensor of claim 1, wherein the synchronization code pattern includes at least one aperture in the strip, the at least one aperture defining one or more of the optically transparent positions.

3. The biosensor of claim 1, wherein the synchronization code pattern has a length, the calibration code pattern having the same length as the synchronization code pattern.

4. The biosensor of claim 1, wherein the positions forming the calibration code pattern are linearly disposed on the strip parallel to the synchronization code pattern.

5. The biosensor of claim 1, wherein the port-insertion region includes a first edge and an opposing second edge, the calibration code pattern being oriented parallel to and along the first edge, the synchronization code pattern being oriented parallel to and along the second edge.

6. The biosensor of claim 5, wherein the synchronization code pattern includes apertures disposed in the strip along the second edge, each of the apertures being generally rectangular with only three sides of the apertures being defined by the strip.

7. The biosensor of claim 1, wherein the calibration code pattern occupies less than 0.04 square inches of a top surface of the strip.

8. The biosensor of claim 1, wherein the synchronization code pattern occupies less than 0.04 square inches of a top surface of the strip.

9. The biosensor of claim 1, wherein the calibration code pattern and the synchronization code pattern together occupy less than 0.06 square inches of a top surface of the strip.

10. The biosensor of claim 1, wherein the biosensor is an optical biosensor.

11. The biosensor of claim 1, wherein the synchronization code pattern has evenly distributed serial openings each separated by evenly distributed optically non-transparent material.

12. The biosensor of claim 1, wherein the biosensor includes a reagent, the reagent including glucose oxidase or glucose dehydrogenase.

13. A biosensor for determining an analyte concentration in a fluid sample, the biosensor comprising:
   a strip including a fluid-receiving area, a port-insertion region, and one or more electrical contacts at least partially disposed within the port-insertion region, the electrical contacts configured to allow a transfer of electrical signals following insertion of the port-insertion region into a receiving port of an analyte meter; and
   a synchronization code pattern disposed within a first area of the port-insertion region that is different from a second area containing a serial calibration code pattern, the synchronization code pattern including optically transparent portions allowing light waves to be transmitted therethrough,
   wherein the synchronization code pattern provides synchronization of the serial calibration code pattern during insertion of the port insertion region into the receiving port.

14. The biosensor of claim 13, wherein the synchronization code pattern has evenly distributed serial openings each separated by evenly distributed optically non-transparent material.

15. The biosensor of claim 13, wherein the biosensor includes a reagent, the reagent including glucose oxidase or glucose dehydrogenase.

16. The biosensor of claim 13, wherein the synchronization code pattern occupies less than 0.04 square inches of a top surface of the strip.

17. The biosensor of claim 13, wherein the calibration code pattern and the synchronization code pattern together occupy less than 0.06 square inches of a top surface of the strip.

18. The biosensor of claim 13, wherein the biosensor is an optical biosensor.

19. The biosensor of claim 13, wherein the calibration code pattern has a length, the synchronization code pattern having the same length as the calibration code pattern.

20. The biosensor of claim 13, wherein the positions forming the calibration code pattern are linearly disposed on the strip parallel to the synchronization code pattern.

* * * * *